(12) United States Patent  (10) Patent No.: US 6,678,897 B2
Lindgren                       (45) Date of Patent:     Jan. 20, 2004

(54) HEARING PROTECTION DEVICE

(75) Inventor: Mats Lindgren, Vikmanshyttan (SE)

(73) Assignee: Ab Kompositprodukter Vikmanshyttan, Vikmanshyttan (SE)

(*) Notice: Subject to any disclaimer, the term of this patent is extended or adjusted under 35 U.S.C. 154(b) by 0 days.

(21) Appl. No.: 10/203,277
(22) PCT Filed: Feb. 14, 2001
(86) PCT No.: PCT/SE01/00302
  § 371 (c)(1),
  (2), (4) Date: Aug. 8, 2002
(87) PCT Pub. No.: WO01/60293
  PCT Pub. Date: Aug. 23, 2001

(65) Prior Publication Data
  US 2003/0037366 A1 Feb. 27, 2003

(30) Foreign Application Priority Data
  Feb. 15, 2000 (SE) .............................................. 0000465

(51) Int. Cl.⁷ ................................................. A42B 1/06
(52) U.S. Cl. ............................. 2/209; 381/383; 181/129
(58) Field of Search ...................... 2/209, 423; 181/129; 128/866; 381/383, 379, 370, 378, 374, FOR 149; 379/430

(56) References Cited

U.S. PATENT DOCUMENTS

| 2,801,423 | A | * | 8/1957 | Shaw et al. | 2/209 |
| 3,016,054 | A | * | 1/1962 | Rosenblatt | |
| 3,719,954 | A | * | 3/1973 | Beguin | 2/209 |
| 4,404,434 | A | * | 9/1983 | Pelt et al. | 381/383 |
| 4,517,418 | A | * | 5/1985 | Baran et al. | 381/378 |
| 6,353,938 | B1 | * | 3/2002 | Young | 2/209 |

FOREIGN PATENT DOCUMENTS

GB        791660       *   3/1958

* cited by examiner

Primary Examiner—Rodney M. Lindsey
(74) Attorney, Agent, or Firm—Sughrue Mion, PLLC

(57) ABSTRACT

Ear defenders comprising an elastic headband (1) and an ear muff (4) arranged on the inside of each leg (2) of the headband. The ear muffs (4) are arranged displaceably along the insides of the legs (2) from the end positions of the legs and so far along the legs that the free ends (7) of the latter can be bent towards and connected to one another, so that the legs completely surround the ear muffs (4). This means that the ear defenders can be compressed before storage in, for example, a pocket.

10 Claims, 14 Drawing Sheets

US 6,678,897 B2

HEARING PROTECTION DEVICE

FIELD OF THE INVENTION

The present invention relates to ear defenders comprising an elastic headband and an ear muff arranged on the inside of each leg of the headband.

BACKGROUND OF THE INVENTION

Ear defenders of this type are widely used all over the world for shutting out noise from the surroundings when noise levels are high. During certain periods of time, the noise level may drop, so that it is preferable not to use the ear defenders. A problem in this connection is how and where to keep the ear defenders, so that they are easily accessible when they are to be used again.

Known ear defenders exist in which this problem has been solved by virtue of the ear defenders being made in such a manner that, when the defenders are not being used, the ear muffs can be folded in, so that they are accommodated inside the headband, after which the defenders as a whole can be put into a pocket. Examples of such ear defenders are disclosed in DE 3332294, CH 534510 and CH 662052. In the case of all these defenders, the function described is achieved by virtue of the ear muffs being connected to the headband via articulated arms.

A disadvantage of these constructions is that the headband then becomes more complicated to manufacture as it consists of a number of parts which have to be assembled in separate operations. The cost of these headbands is thus obviously greater than that of headbands which are manufactured in one piece.

GB 791660 describes ear defenders in which the ear muffs are fastened to the headband by means of a wing nut and a ball joint. Several manufacturing and assembly operations are required, and the defenders obtained cannot be compressed to the necessary extent to be easily put into a pocket or equivalent.

THE OBJECT OF THE INVENTION

One object of the present invention is to produce ear defenders with a headband made in one piece, in which the ear muffs are mounted directly, allowing the headband, when the ear defenders are not being used, to be compressed and completely surround the ear muffs.

Another object is to produce ear defenders of this type which can be manufactured at very low cost.

According to the present invention, the above-mentioned aims are achieved by means of ear defenders of the type indicated in the first paragraph, in which the ear muffs are arranged displaceably along the insides of the legs from the ends of the legs and so far along the legs that the free ends of the latter can be bent towards and connected to one another, so that the legs completely surround the ear muffs.

Ear defenders of this type can, when not being used, be compressed to such an extent that they can be kept in, for example, a pocket. They can also be manufactured at very low cost.

It is preferred that the legs are made with longitudinal slots and that the ear muffs have guide elements running in the slots. By making the guide elements so that they are rotatable in the slots, the muffs can be rotated in relation to the headband, which inter alia allows the headband to be arranged over the top of the head or around the back of the head as desired by the wearer.

The free end of at least one leg is suitably shaped in such a manner that it can be inserted into and locked in an opening in the other leg. In this way, the headband can be kept compressed the whole time it is not being used.

Further features of the invention emerge from the following patent claims.

The invention will be described in greater detail below with reference to the embodiments shown by way of example in the accompanying drawings.

DETAILED DESCRIPTION OF THE PREFERRED EMBODIMENTS

Figure 1:
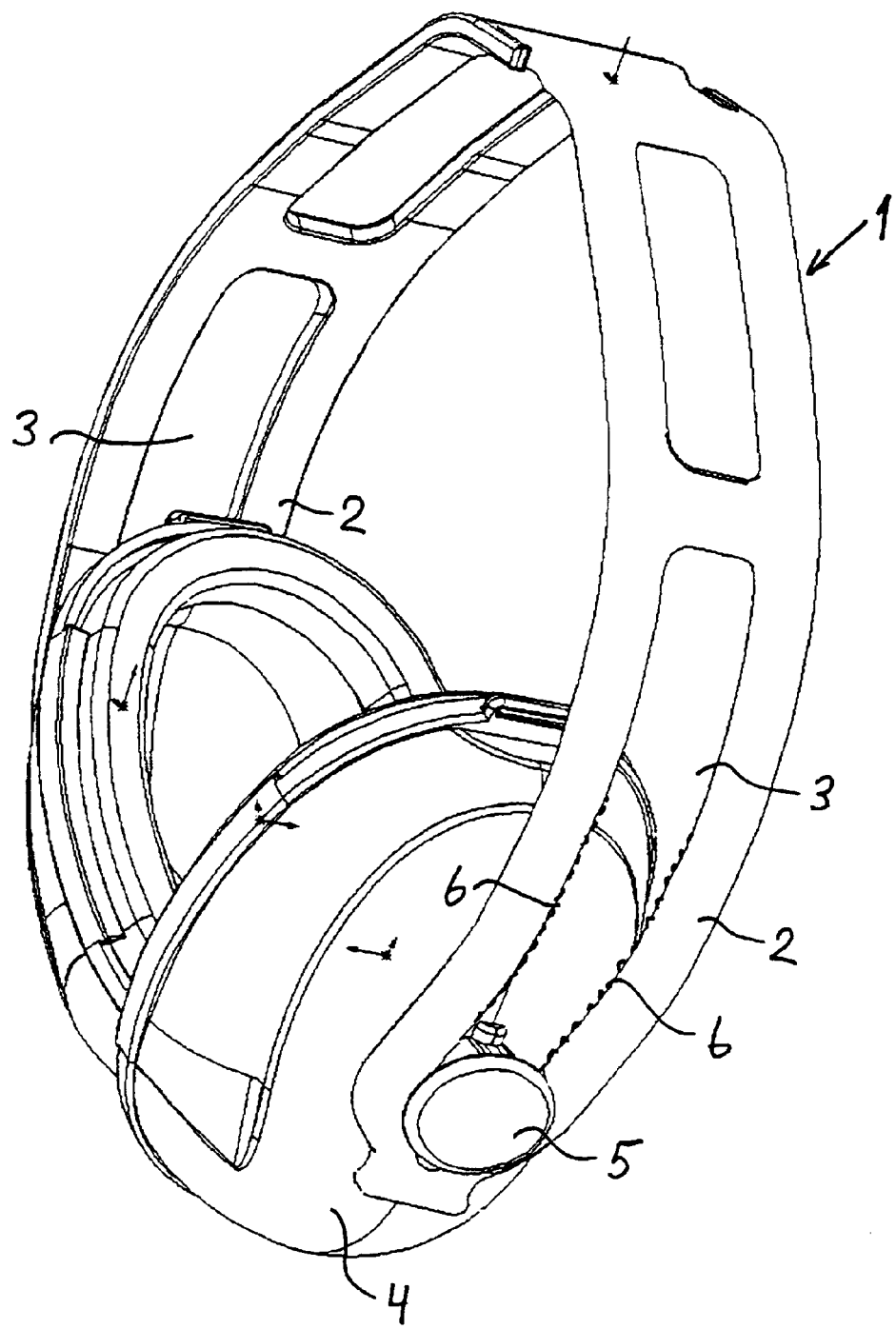
FIG. 1 shows a headband with ear muffs according to the invention.
Figure 2:
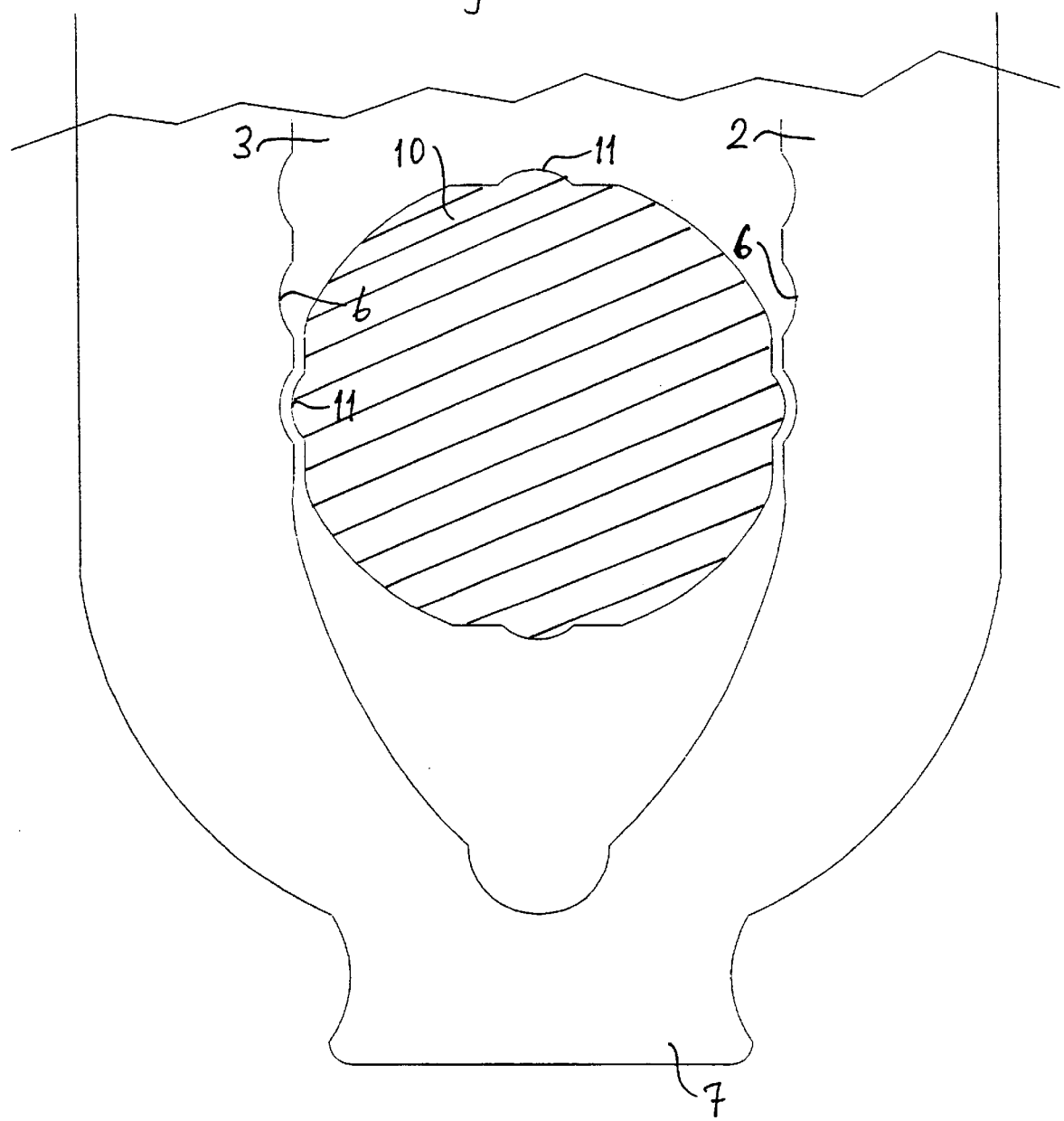
FIG. 2 shows a part of the headband according to FIG. 1.

The ear defenders according to FIG. 1 comprise a headband 1 made of an elastic plastic material manufactured in one piece. The legs 2 of the headband are each provided with a longitudinal slot 3. The legs 2 bear ear muffs 4 which are arranged on the inside of the legs and can be designed in a manner known per se. The muffs 4 are each made with a guide element which projects through the respective slot 3 and is retained in the slot by means of an enlarged portion 5. This can be seen from FIG. 2, which shows a part of one leg 2 of the headband with a guide element 10 received in the slot 3. The guide elements 10 suitably have a square cross section with rounded edges and can be made with projecting ridges 11 which fit in recesses 6 in the edges of those portions of the legs 2 which delimit the slots 3.

Figure 3:
FIGS. 3 and 4 illustrate two different positions during use of ear defenders according to FIG. 1.
Figure 4:
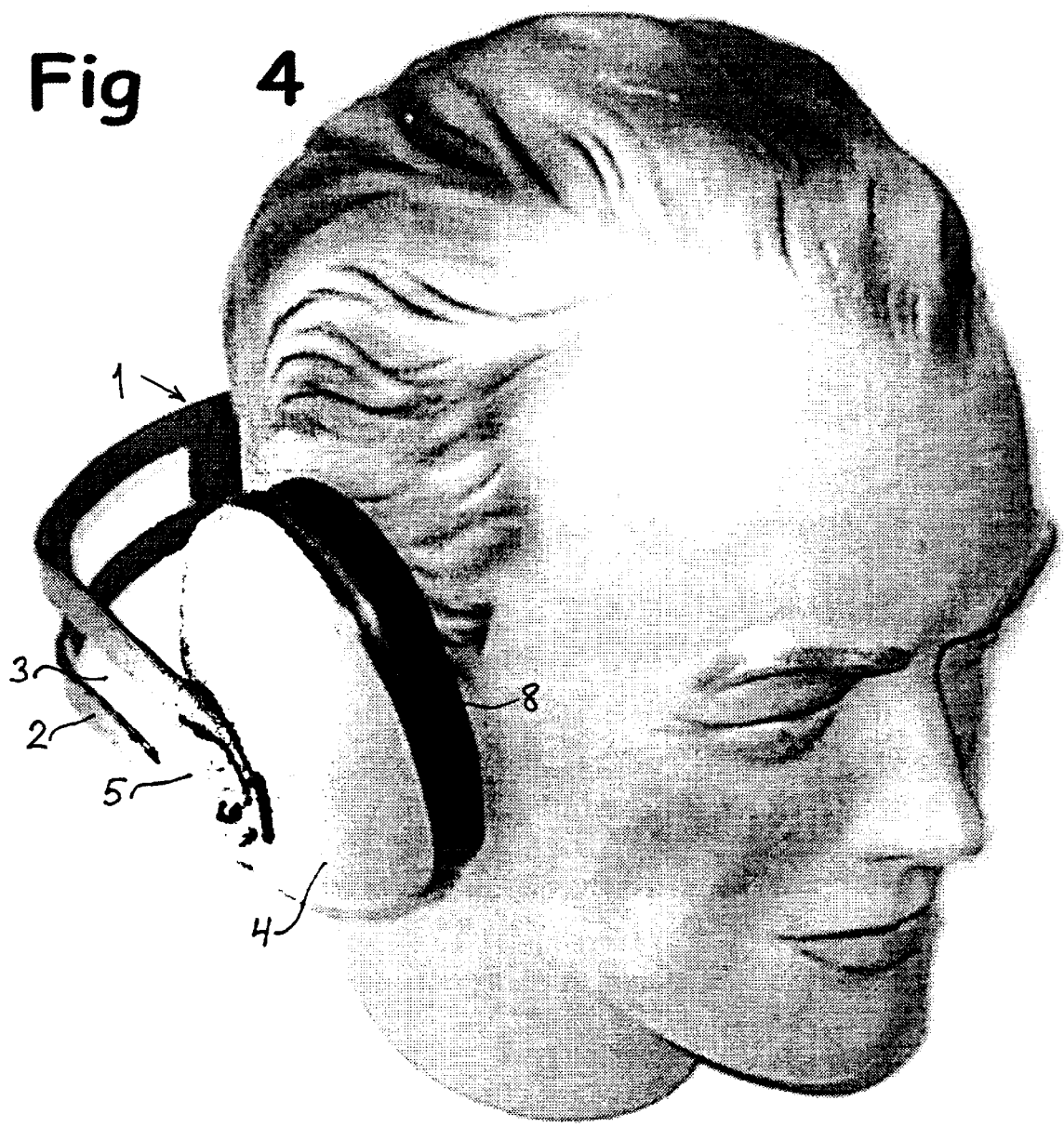

The recesses 6 allow the ear muffs to be displaced and adjusted into different positions so as to fit the head size of the wearer. The guide elements 10 of the ear muffs 4 also allow the muffs to be rotated with their guide elements 10 in the slots 3 of the legs 2 into different rotary positions. This allows inter alia the ear muffs 4 to maintain the intended orientation relative to the ears and the head (see FIGS. 3 and 4) irrespective of whether the headband 1 is worn over the top of the head or behind the back of the head. This allows the wearer a considerable range of options.

Figure 5:
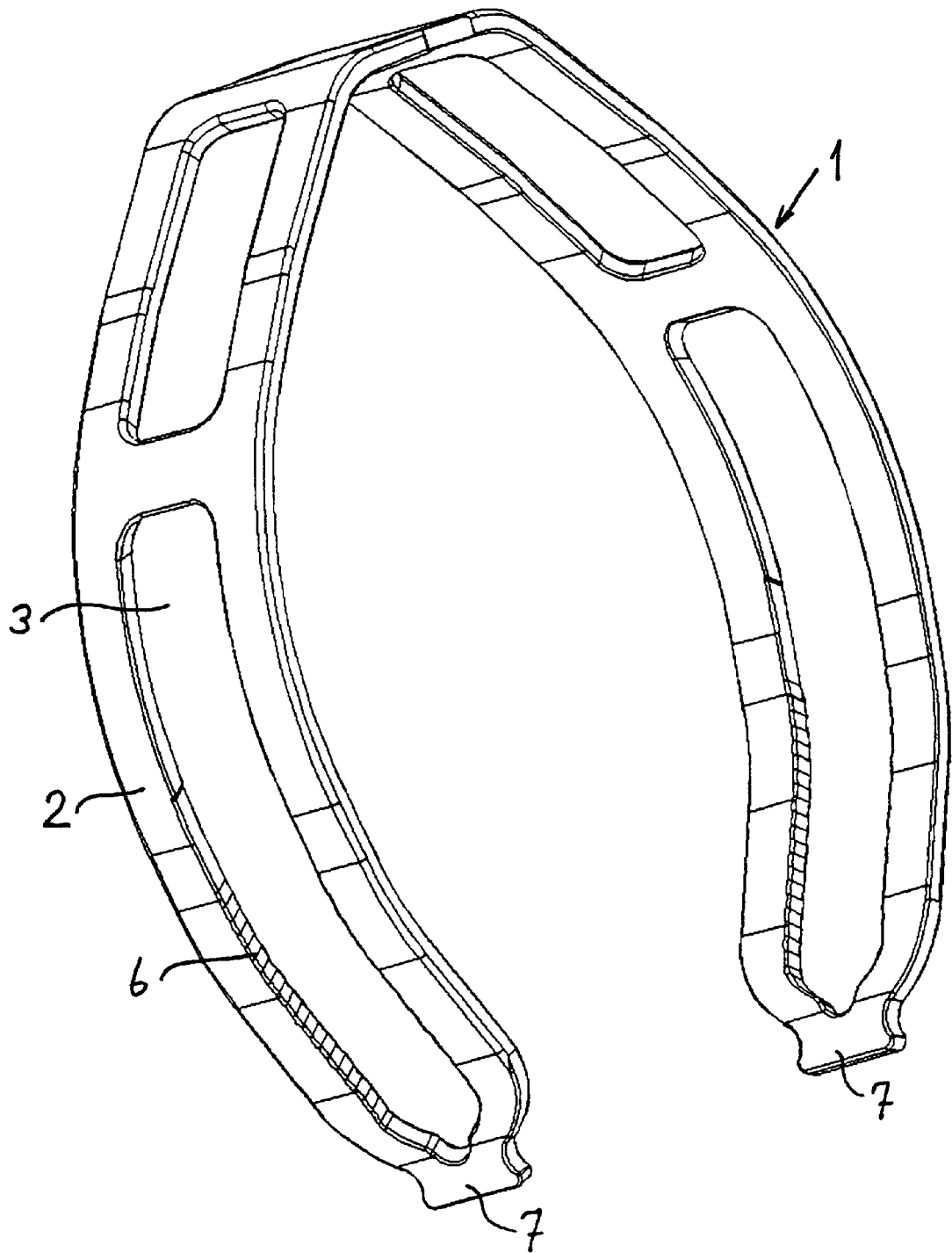
FIG. 5 shows the headband in the open state.
Figure 6:
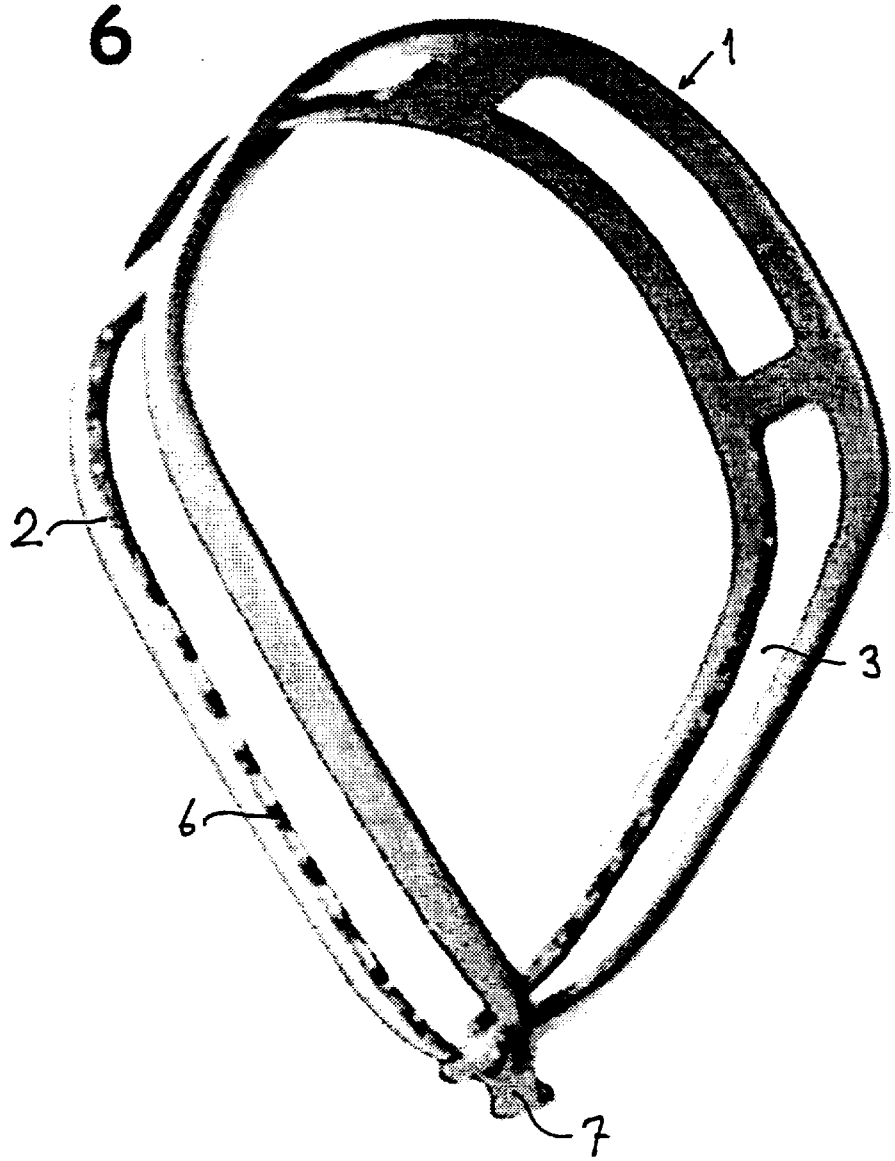
FIG. 6 shows the headband in the clasped-together state.

It can be seen from FIG. 5 that the free end portions 7 of the legs 2 of the headband 1 are made in the form of hooks located in the plane of the headband. This allows the hook-shaped end portion of one leg 2 to be inserted into the slot 3 in the opposite leg with a certain amount of turning, so that, after release, the legs are locked together relative to one another, as illustrated in FIG. 6.

In this case, both the end portions of the headband 1 are identical, which means that either of the legs 2 can be inserted into the opposite leg. Alternatively, only one leg can be made with a hook-shaped projection, and the other can be made with an opening intended for receiving the projection.

Figure 7:
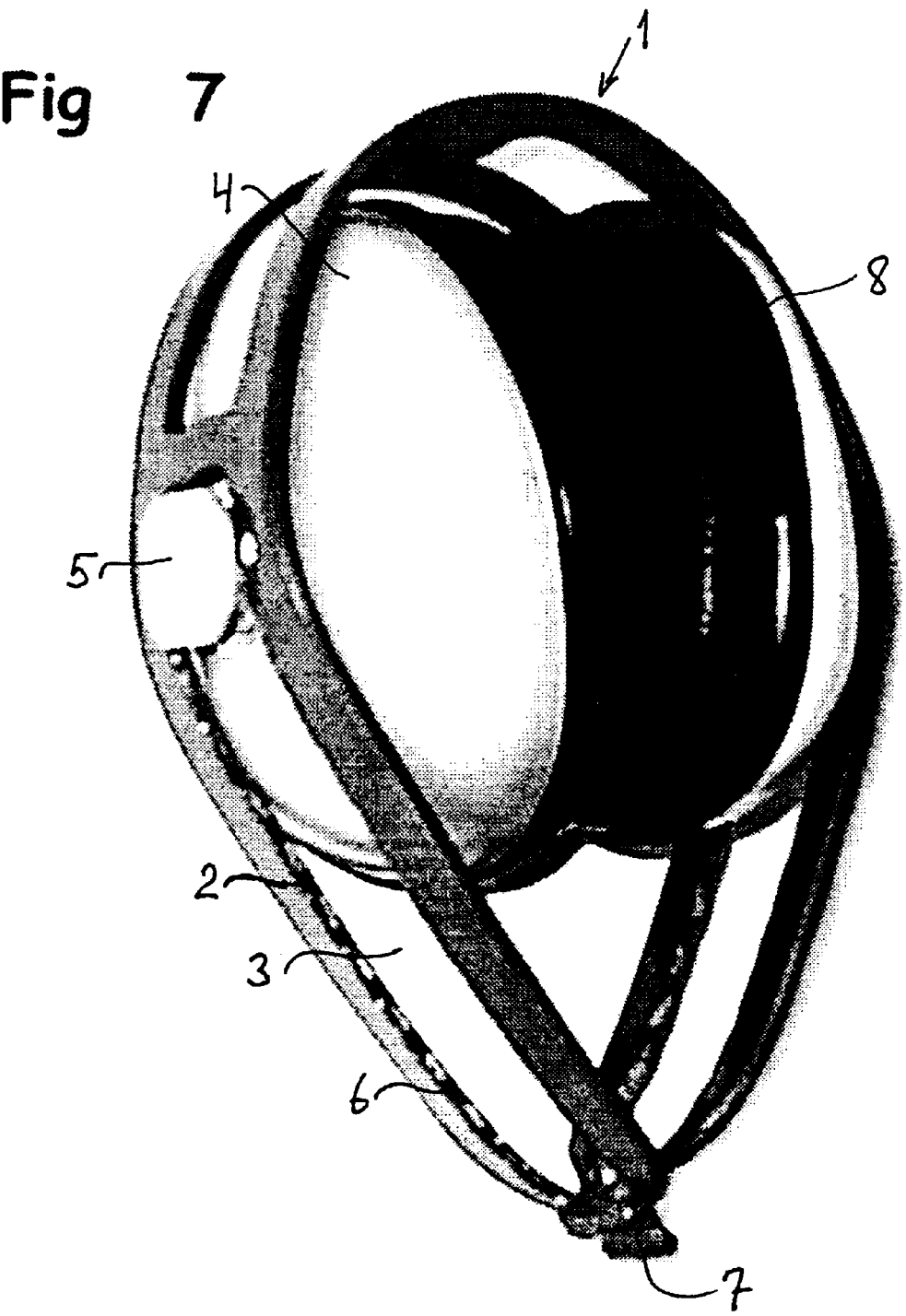
FIG. 7 shows the ear defenders according to FIG. 1 with the headband clasped together.

The slots 3 in the legs 2 are so long that the ear muffs 4 can be pushed up so far along the inner surface of the respective leg that the end portions of the legs can be locked together, as shown in FIG. 7. In this position, the ear muffs 4 are completely surrounded by the headband 1, and the ear defenders have at the same time been compressed to such an extent that they can easily be put into a pocket or equivalent. Those parts of the legs 2 of the headband which project beyond the ear muffs 4 can serve as a handle which facilitates handling of the compressed ear defenders, which is an advantage if the wearer is using stout gloves.

As can be seen from FIG. 7, when the ear defenders are compressed, the ear muffs 4 will also be pressed against one another, so that the elastic comfort rings arranged on the ear muffs are pressed against one another. These are then protected against dirtying and seal the inner cavity in each ear muff which is to accommodate an ear.

In certain situations, there is a need to be able to carry ear defenders, which are not being used, about the person in a simple manner without putting them in a pocket or equivalent. For this purpose, use is sometimes made of special waist-belt hooks, on which the ear defenders can be hung. However, this requires manufacture, stocking and mounting of a separate element.

Figure 8:
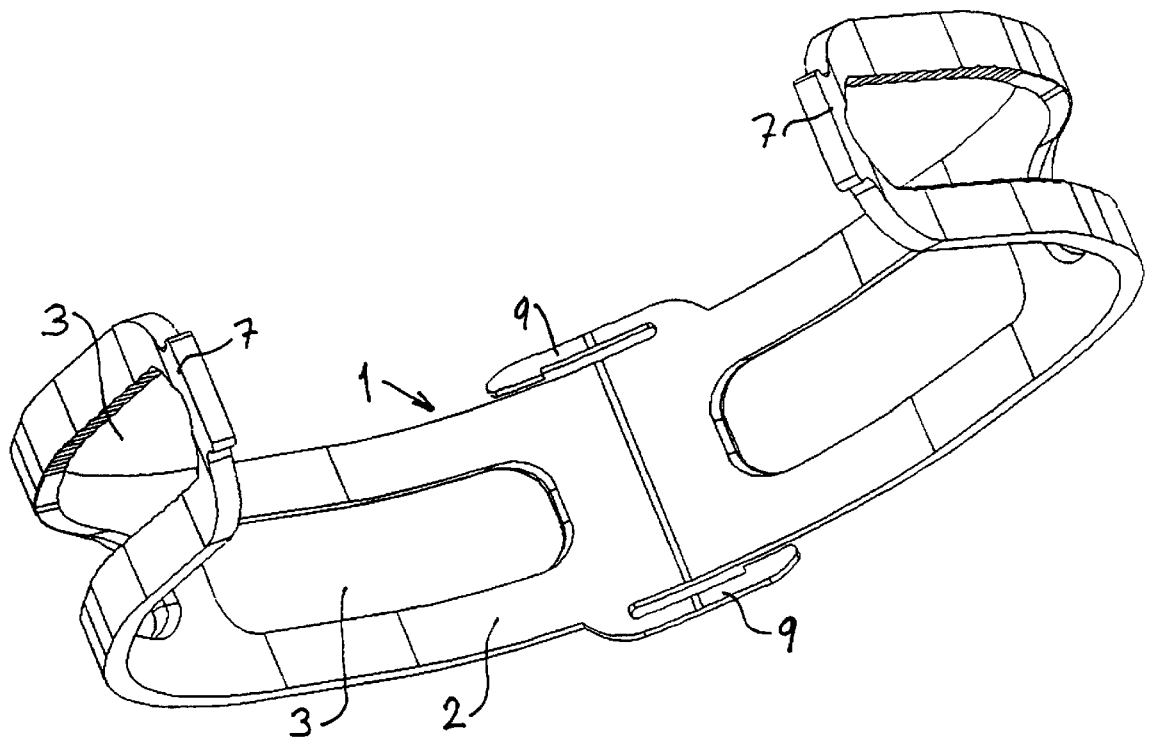
FIGS. 8 and 9 show an alternative embodiment of a headband according to the invention.
Figure 9:
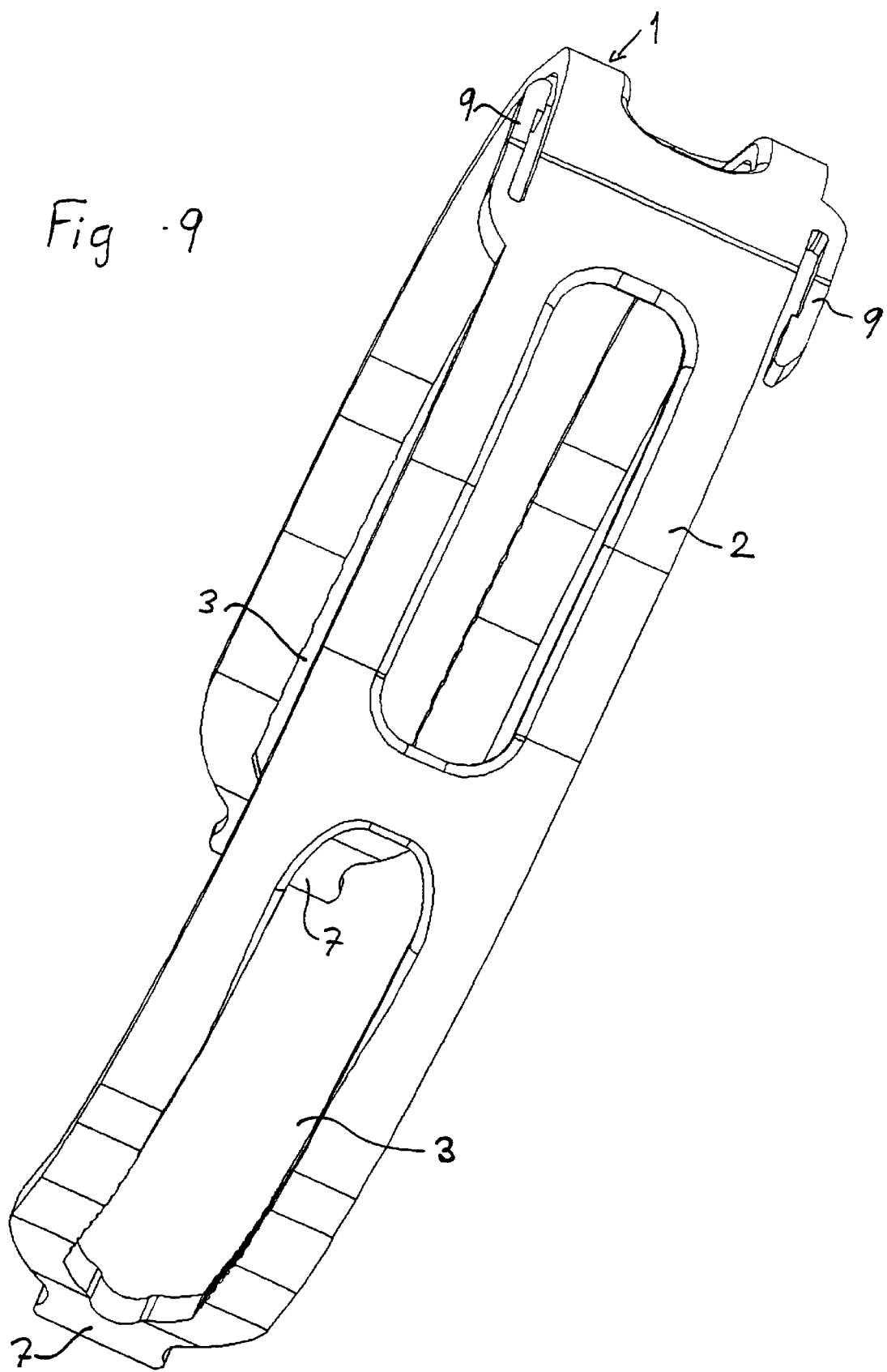

According to the present invention, this problem can be solved by providing the headband 1 itself with an integral hanging arrangement, suitably in the form of a hook-shaped element 9 (see FIGS. 8 and 9). Such a hook-shaped element, which is integral with the remainder of the headband, can be produced without extra cost in connection with the injection moulding of the headband as a whole. The entire headband with the hanging hook 9 is therefore manufactured in a single operation, and it is not necessary to deal with or mount a separate hanging arrangement.

Figure 10:
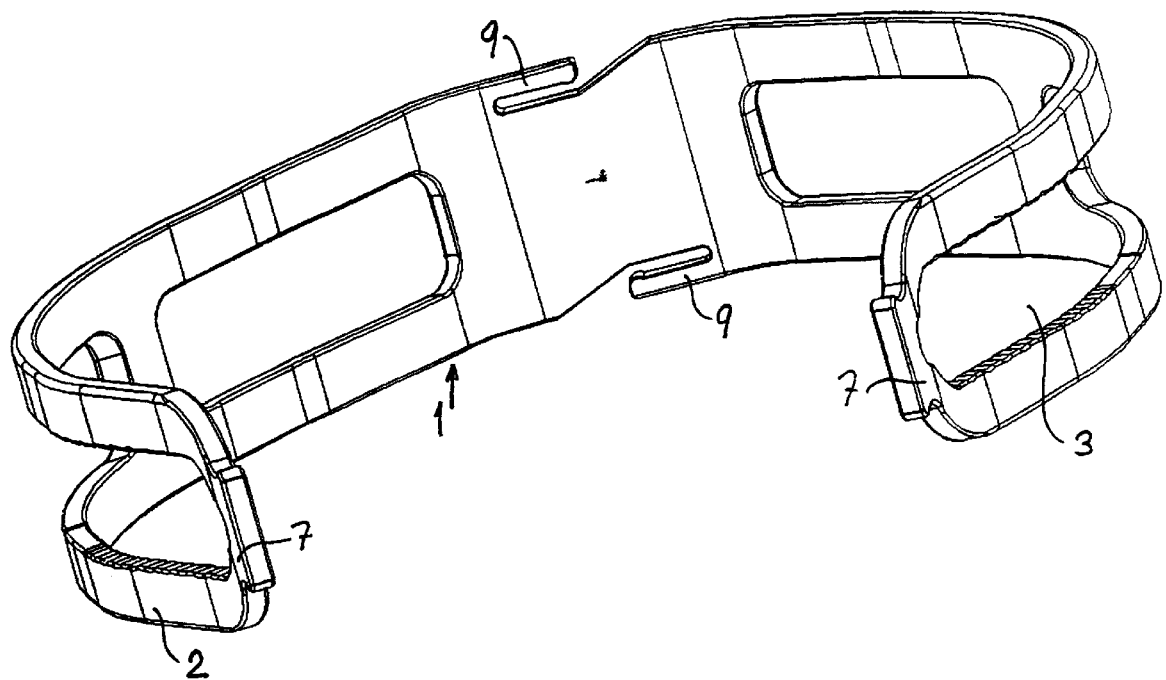
FIG. 10 shows a further embodiment of the headband.

FIG. 10 shows an alternative embodiment of a headband 1 according to FIGS. 8 and 9, the hanging hook 9 having been moved in, so that it does not project beyond the side edge of the headband. This reduces the risk of the hook 9 accidentally catching on anything.

Figure 11:
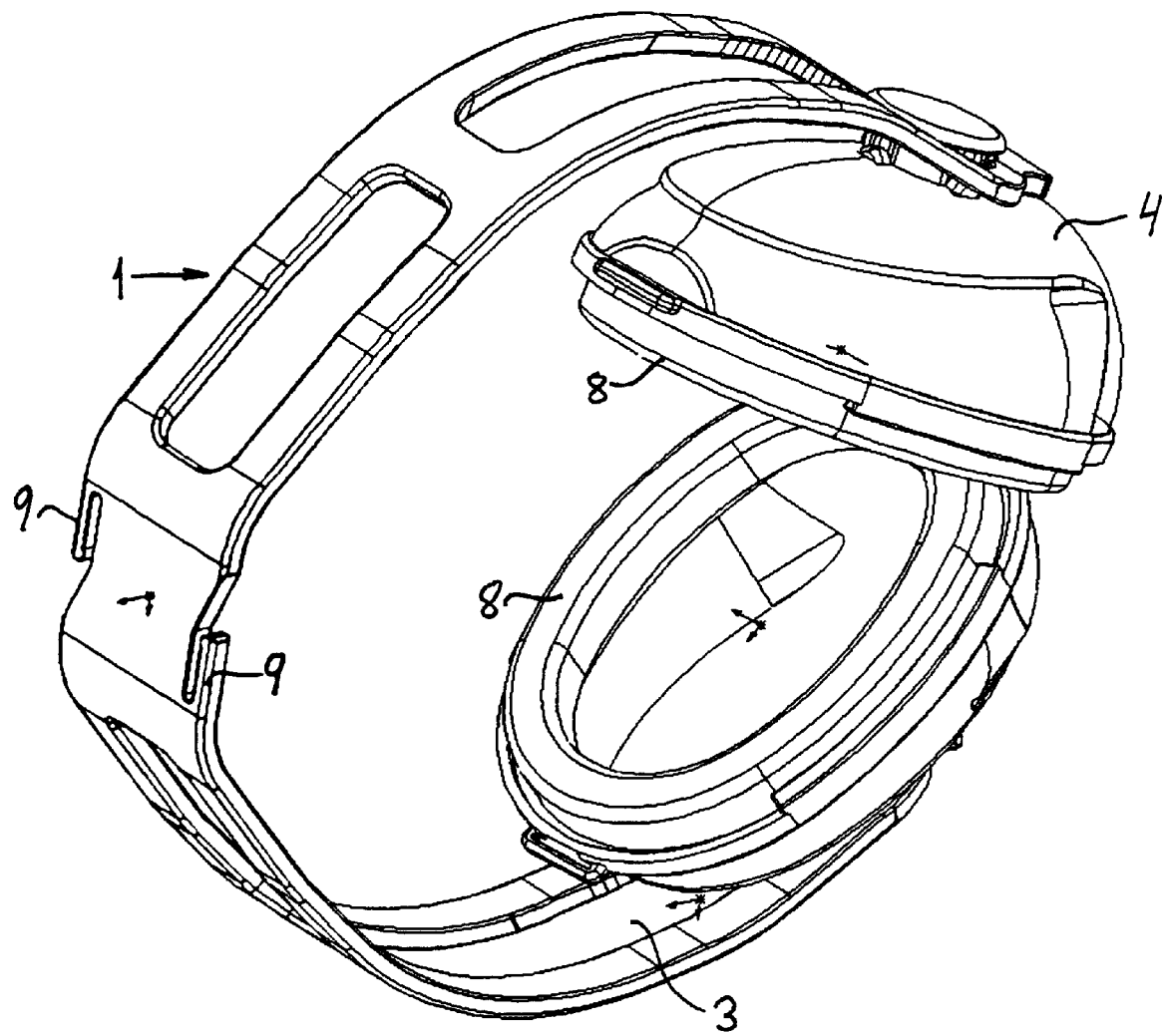
FIGS. 11–13 show ear defenders with a headband according to FIG. 10 in different views.
Figure 12:
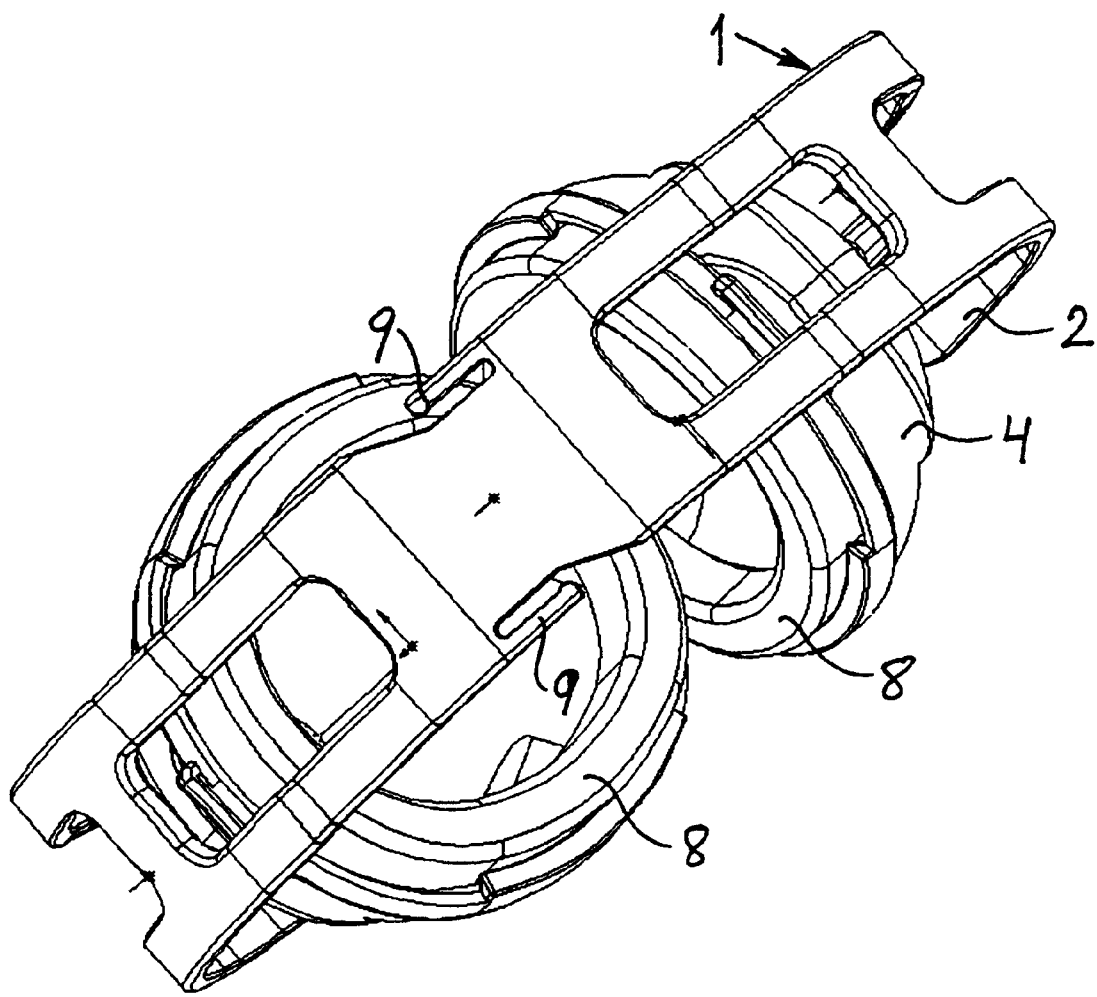
Figure 13:
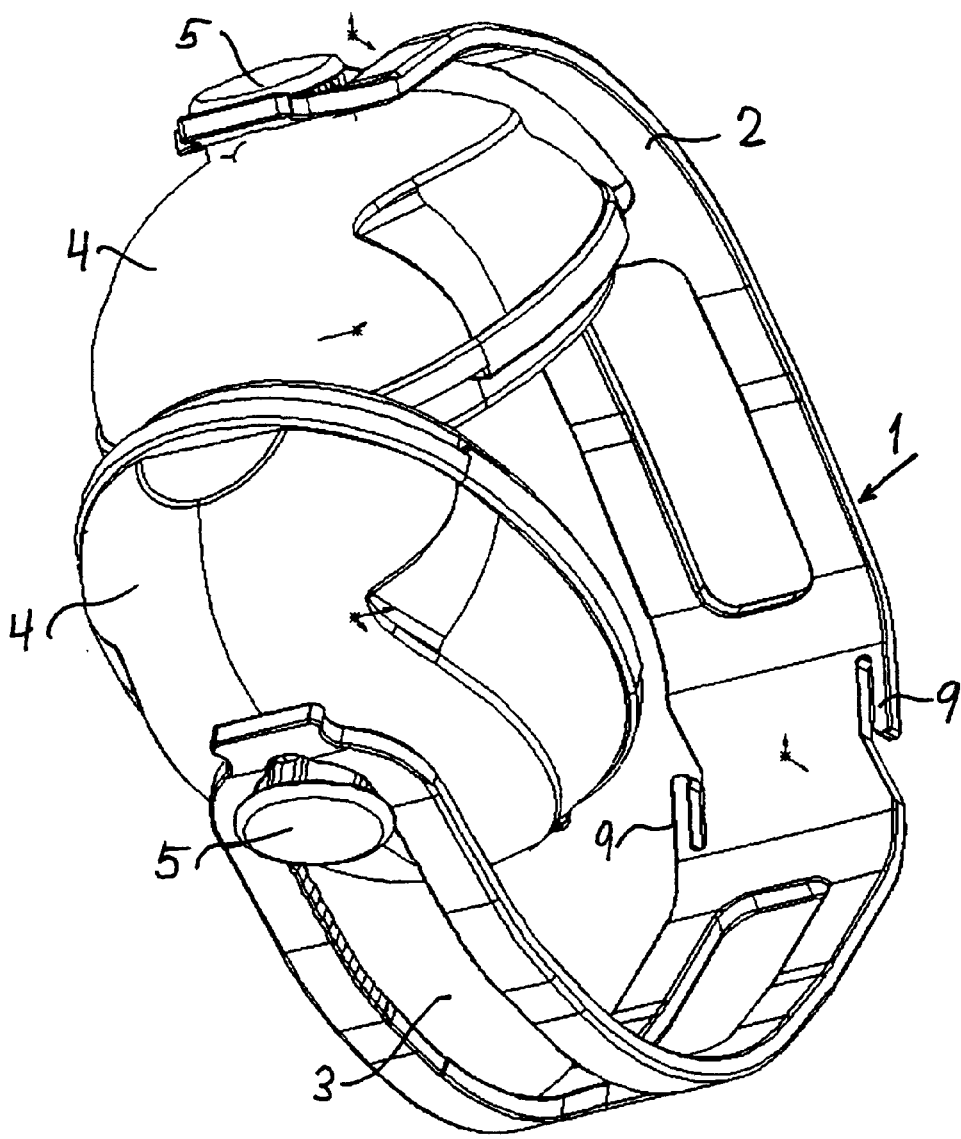

FIGS. 11–13 show different views of ear defenders according to the invention which make use of a headband according to FIG. 10.

Figure 15:
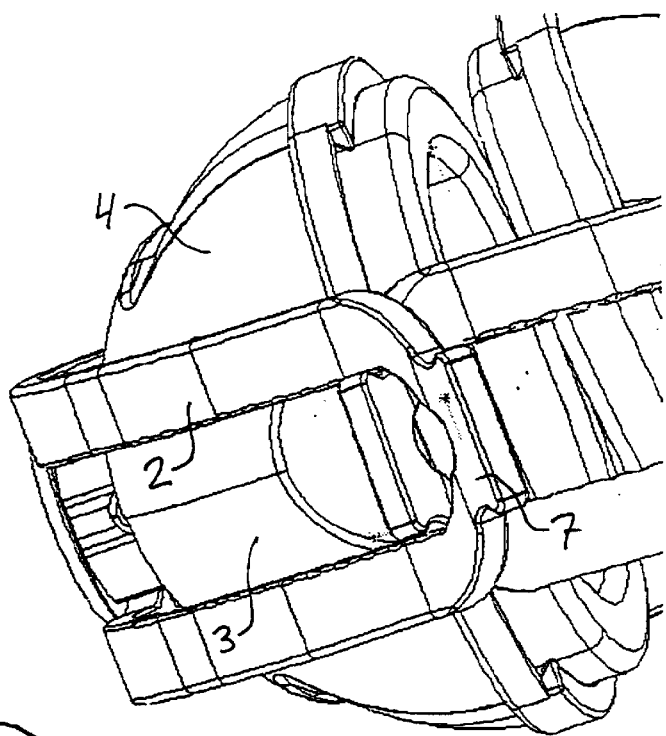
FIGS. 14 and 15 show ear defenders according to FIGS. 11–13 with the headband clasped together.
Figure 14:
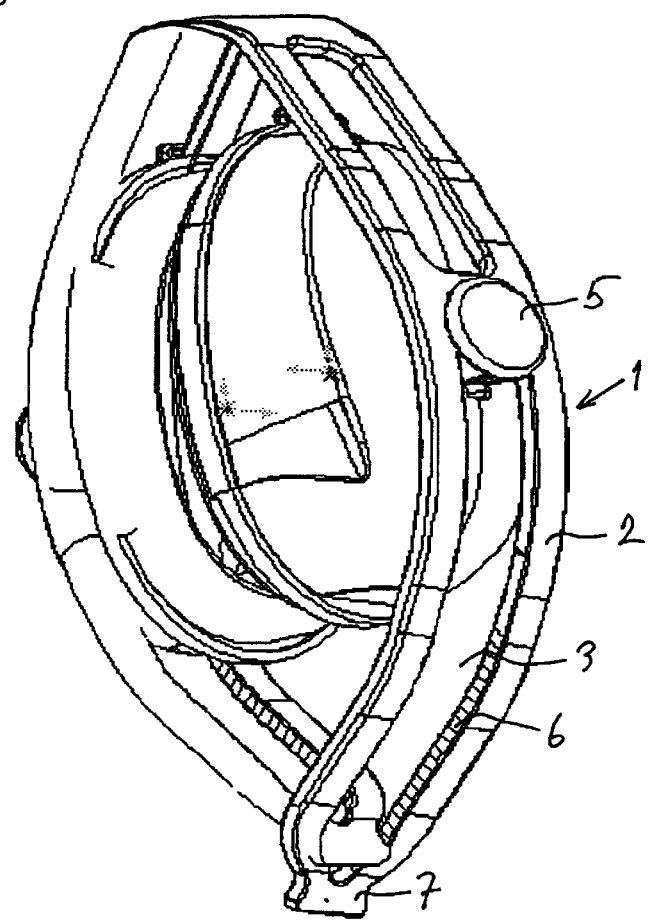

FIGS. 14 and 15 show ear defenders according to FIGS. 11–13 in the compressed position, that is to say a position in which the ear muffs 4 have been pushed up along the legs 2 of the headband 1, so that it has been possible to lock the free ends of the legs together in order to compress the ear defenders when they are not being used.

The invention has been described above in connection with the embodiments shown in the drawings. However, these can be varied in a number of respects within the scope of the patent claims, inter alia with regard to the exact embodiment of the headband and its slots and openings. The coupling between the displaceable ear muffs and the headband can also be varied in various respects without departing from the inventive idea. This is also true of the means for holding the legs of the headband together.

What is claimed is:

1. Ear defenders comprising an elastic headband (1) and an ear muff (4) arranged on the inside of each leg (2) of the headband, characterized in that the ear muffs (4) are arranged displaceably along the insides of the legs (2) from the end portions of the legs and so far along the legs that the free ends (7) of the latter can be bent towards and connected to one another, so that the legs completely surround the ear muffs (4).

2. Ear defenders according to claim 1, characterized in that the legs (2) are made with longitudinal slots (3) and in that the ear muffs (4) have guide elements (10) running in the slots.

3. Ear defenders according to claim 2, characterized in that the muffs (4) are rotatable with their guide elements (10) in the slots (3).

4. Ear defenders according to claim 2, characterized in that the free end (7) of one leg (2) is shaped in such a manner that it can be inserted into and locked in an opening (3) in the other leg (2).

5. Ear defenders according to claim 4, characterized in that the free ends (7) of both the legs (2) are made with hook-shaped portions which can be inserted into and locked in the slot (3) of the opposite leg.

6. Ear defenders according to claim 5, characterized in that the headband (1) is made in one piece in the form of a curved band made of an elastic plastic material and in that the hook-shaped end portions (7) are located in the plane of the band.

7. Ear defenders according to claim 2, characterized in that the slots (3) are made with adjustment notches (6) for fixing said guide elements (10) projecting from the ear muffs (4).

8. Ear defenders according to claim 7, characterized in that the guide elements (10) running in the slots (3) of the legs (2) each have an essentially square cross section and an enlarged end portion (5).

9. Ear defenders according to claim 1, characterized in that the headband (1) is made in one piece in the form of a curved band made of an elastic plastic material and in that the band is made with integral hanging means (9).

10. Ear defenders according to claim 9, characterized in that said hanging means (9) are in the form of hooks formed in the plane of the band and along the outer edges of the latter.

* * * * *